(12) United States Patent
Gester et al.

(10) Patent No.: US 11,062,544 B2
(45) Date of Patent: Jul. 13, 2021

(54) DISTRIBUTED SYSTEM FOR ACCESS CONTROL AND SOBRIETY TESTING

(71) Applicant: SENSEAIR AB, Delsbo (SE)

(72) Inventors: Raimo Gester, Västerås (SE); Johan Wiklander, Västerås (SE)

(73) Assignee: Senseair AB, Delsbo (SE)

( * ) Notice: Subject to any disclaimer, the term of this patent is extended or adjusted under 35 U.S.C. 154(b) by 0 days.

(21) Appl. No.: 16/628,394

(22) PCT Filed: Jul. 6, 2018

(86) PCT No.: PCT/SE2018/050746
§ 371 (c)(1),
(2) Date: Jan. 3, 2020

(87) PCT Pub. No.: WO2019/009798
PCT Pub. Date: Jan. 10, 2019

(65) Prior Publication Data
US 2020/0219350 A1 Jul. 9, 2020

(30) Foreign Application Priority Data
Jul. 7, 2017 (SE) .................................. 1750893-8

(51) Int. Cl.
*G07C 9/38* (2020.01)
*G07C 9/37* (2020.01)
(Continued)

(52) U.S. Cl.
CPC ............... *G07C 9/38* (2020.01); *A61B 5/082* (2013.01); *A61B 5/18* (2013.01); *A61B 5/4845* (2013.01);
(Continued)

(58) Field of Classification Search
CPC ....................................................... G07C 9/38
See application file for complete search history.

(56) References Cited

U.S. PATENT DOCUMENTS

| 3,780,311 A | 12/1973 | Brown | |
| 7,042,334 B2 * | 5/2006 | Mosgrove | E05B 19/0005 340/5.73 |

(Continued)

FOREIGN PATENT DOCUMENTS

AU 2015101831 A4 2/2016

OTHER PUBLICATIONS

International Search Report and Written Opinion dated Sep. 17, 2018, issued in corresponding International Patent Application No. PCT/SE2018/050746.

*Primary Examiner* — K. Wong
(74) *Attorney, Agent, or Firm* — Morgan, Lewis & Bockius LLP

(57) ABSTRACT

The invention relates to a distributed system (1; 11; 21) for access control and sobriety testing comprising an authorization control and sobriety testing station (2; 12; 22; 32), which obtains authorization data and a bodily signature sample from an individual seeking access, a central control unit (3; 13; 23; 33), which, if there is a positive verification of the authorization data and no detection of alcohol in the bodily signature sample, issues temporary authorization information, and at least one access control unit (4; 14; 24), which obtains the temporary authorization information and, upon a positive verification of the temporary authorization information, grants access to the individual who is seeking such access.

19 Claims, 7 Drawing Sheets

(51) Int. Cl.
*A61B 5/08* (2006.01)
*A61B 5/18* (2006.01)
*A61B 5/00* (2006.01)
*B60W 40/08* (2012.01)

(52) U.S. Cl.
CPC .............. *B60W 40/08* (2013.01); *G07C 9/37* (2020.01); *A61B 2503/22* (2013.01); *B60W 2040/0836* (2013.01); *B60W 2040/0854* (2013.01)

(56) References Cited

U.S. PATENT DOCUMENTS

| | | | |
|---|---|---|---|
| 7,823,681 B2 | 11/2010 | Crespo et al. | |
| 9,026,267 B2* | 5/2015 | Schwarz | G05D 1/0022 |
| | | | 701/2 |
| 9,562,889 B2* | 2/2017 | Son | G01N 33/0008 |
| 9,746,456 B2* | 8/2017 | Keays | G01N 33/497 |
| 10,390,732 B2* | 8/2019 | Ross | A61B 5/0004 |
| 10,491,729 B2* | 11/2019 | DeBates | G08B 21/18 |
| 10,596,903 B2* | 3/2020 | DeVries | B60R 25/002 |
| 2013/0021153 A1 | 1/2013 | Keays | |

* cited by examiner

DISTRIBUTED SYSTEM FOR ACCESS CONTROL AND SOBRIETY TESTING

FIELD OF THE INVENTION

The present invention relates generally to a system for access control and sobriety testing, and more particularly to a distributed system for access control and sobriety testing comprising an authorization control and sobriety testing station, which obtains authorization data and a bodily signature sample from an individual seeking access, a central control unit, which, based on no detection of alcohol in the bodily signature sample and a positive verification of the authorization data, issues temporary authorization information, and at least one access control unit, which obtains the temporary authorization information and, upon a positive verification of the temporary authorization information, grants access to the individual who is seeking access. The invention relates also to a corresponding method for access control and sobriety testing.

BACKGROUND OF THE INVENTION

Today, it is increasingly common to equip cars, buses, trains, trucks, lorries and other vehicles with a breath alcohol ignition interlock, which, in an interlocking state, interrupts an electric signal from the ignition to the starter motor of the vehicle in question. The breath alcohol ignition interlock typically comprises a breath analyzer installed in a vehicle, and when a driver attempts to start the vehicle, he or she is first requested to blow into a mouthpiece arranged at and connected to the breath analyzer, whereupon the breath analyzer analyses the breath sample for presence of alcohol or other substances, and if no alcohol (or only a legally acceptable amount of alcohol) is detected, the interlock of the ignition is removed such that the vehicle can be started as normal.

An exemplifying breath alcohol ignition interlock of this type is disclosed in the U.S. Pat. No. 3,780,311 to Brown, wherein a breath alcohol detector comprises a fast-acting, solid-state sensor, which is responsive to the exposure of alcohol to produce a first electric signal, and a pressure-sensitive switch, which is responsive to the application of a breath sample to produce a second electric signal, and a logic circuitry, which is interconnected with the automobile starter to prohibit operation until the logic circuitry has received a proper combination of first and second electric signals.

In a breath alcohol ignition interlock system, it is further known to combine a breath alcohol detector with an identification system, which verifies the identity of a person who seeks access to a vehicle. Such a combined identification and breath alcohol ignition interlock system is, for example, presented in the U.S. Pat. No. 7,823,681 to Crespo et al., wherein biometrical facial features are scanned and matched with a stored facial image of a previously authorized driver, and the interlock system locks the vehicle in question if the scanned facial features cannot be matched with the stored facial image and/or if presence of alcohol is detected by the breath alcohol detector.

A common feature of the known breath alcohol ignition interlock systems is that a system of this kind is implemented as an individually and independently operating system in a specific vehicle. In other words, a typical breath alcohol ignition interlock system can be characterized as a stand-alone apparatus or device, which operates without interaction with other breath alcohol ignition interlock systems, or operates without interaction with other systems and units which perform functions that are normally included in an access control and sobriety testing system. Although this stand-alone feature in many circumstances provides an advantage, it also creates problems in, for example, situations where one driver's failure to start and drive one vehicle negatively influences other drivers' possibilities to drive their vehicles due to formation of a queue behind the failing driver. Further, to manage and operate a large fleet of vehicles, where each vehicle is equipped with a separate breath alcohol ignition interlock system, is also a challenging problem for, e.g., a logistic manager, since there is always an imminent risk that one vehicle cannot be started—be that because of a malfunction of the breath alcohol ignition interlock system itself or that the designated driver actually is under the influence of alcohol. Also, several or recurring delays in the start-up procedures of several breath alcohol ignition interlock systems can aggregate to similar logistical problems, e.g. when many vehicles and drivers are interacting in a traffic situation, or when vehicles are scheduled to start and drive off at specific scheduled times. Such delays can, for example, be temperature dependent due to the warm-up time of the breath analyzer.

Thus, there is a need for a more versatile and robust system, which more effectively and reliable can handle access control and sobriety testing, wherein the system in particular should be capable of handling access control and sobriety testing of a large number of individuals who are seeking access to a large number of vehicles, where the individuals and/or the vehicles are interconnected or interdependent in such a way that one individual's success or failure to start and drive a certain vehicle affects another individual's possibility to drive his/her vehicle, or affects a third party's possibility to carry out his/her work. Such a third party can, for instance, be a logistic manager who administrates a large fleet of vehicles and associated drivers. The system for access control and sobriety testing should also be useful in situations where a number of individuals are seeking access to areas, e.g. access to restricted areas or common areas such as roads. There is also a need for an improved method for access control and sobriety testing, which method provides the corresponding advantages.

SUMMARY OF THE INVENTION

The above-mentioned objects are achieved by the present invention according to the independent claims. Preferred embodiments are set forth in the dependent claims.

The present invention relates generally to a system for access control and sobriety testing, and more specifically to a distributed and preferably non-invasive system for access control and sobriety testing, wherein an authorization control and sobriety testing station obtains authorization data and a bodily signature sample from an individual who is seeking access to, e.g., a vehicle or an area. The authorization and sobriety testing station is configured to analyse the bodily signature sample, which, for example, can be a breath sample or sample based on transdermal alcohol detection, and is further arranged to the detect presence of alcohol in the bodily signature sample, and to send the result of the analysis to a central control unit. Since the system is designed to be user-friendly and to handle many individuals, the system for access control and sobriety testing is preferably a non-invasive system. The authorization control and sobriety testing station is further configured to send the authorization data obtained from the individual who seeks access to the central control unit, which compares the authorization data with general authorization information that previously has been stored in the central control unit, and if a positive match is found between the authorization data and the general authorization information and if there is no detection of alcohol in the bodily signature sample (or detection of alcohol in an amount which is below a predetermined and acceptable limit), the central control unit issues temporary authorization information. The distributed access control and sobriety testing system comprises further at least one access control unit (in practice typically many access control units), which is configured to obtain the temporary authorization information issued by the central control unit and to verify the validity of the temporary authorization information, and is further configured to, based on a positive verification of the validity of the temporary authorization information, grant access to the individual who is seeking such access.

A distributed system is herein defined as a system in which the main functional units can be localized and configured arbitrarily. In the system and method according to the invention the main functional units are the central control unit, the authorization control and sobriety testing station, and the access control unit. According to one aspect of the invention, the units requiring interaction with a user, the authorization control and sobriety testing station and the access control unit are provided at different locations. The user will first encounter the authorization control and sobriety testing station at a first location and at a later stage encounter the access control unit at a second location. The second location may for example be in a vehicle and the access control unit being a mobile unit that communicates with the central control unit via wireless communication.

The distributed access control and sobriety testing system according to the invention is that an authorization control and sobriety testing station in co-operation with a central control unit can issue temporary authorization information to a large number of individuals who are seeking access to, for example, a large number of vehicles. Thus, each of the individuals who has passed the authorization control and sobriety testing station knows that he or she is both sober and authorized to have access to a vehicle, as long as the access control unit, which typically is arranged in a specific vehicle, can verify the validity of the temporary authorization information. And also a third party, e.g. a logistic manager, knows that all individuals who have passed the authorization control and sobriety testing station potentially are available and capable of driving the vehicles. In an embodiment of the invention, verification of the validity of the temporary authorization information includes a control that the temporary authorization information was not issued a too long time before the individual interacts with an access control unit, which verifies the temporal validity of the temporary authorization information by comparing a time identification for when the temporary authorization information was issued with an accurate clock showing the current time. In another embodiment, verification of the validity of the temporary authorization information also includes a repeated check of the authorization data, i.e. a repeated matching of the authorization data with the general authorization information, or a matching of other authorization data (i.e. authorization data that was not utilized by the authorization control and sobriety testing station) with the general authorization information stored in the central control unit, to avoid that one person in an unduly way has got hold of temporary authorization information that was originally issued for another person. In all embodiments of the invention, authorization data can be delivered to an authorization control and sobriety testing station in the form of numbers or characters, etc., which are entered into the authorization control and sobriety testing station by the individual seeking access or which are read by the authorization control and sobriety testing station from, e.g., an RFID card, a driver's license, a passport, or a mobile phone displaying identification data, which the individual presents to the authorization control and sobriety testing station. Alternatively, authorization data can be provided in the form of biometrical data, e.g. in the form of a facial image, a finger print, or eye identification data, which the authorization control and sobriety testing station obtains by scanning the individual who is seeking access.

There are several advantages provided with a distributed system for access control and sobriety testing according to the invention, which will become clear from the description below. As an example, by means of the distributed access control and sobriety testing system according to the invention, a logistic manager knows that each of the drivers who has passed the authorization control and sobriety testing station is at his/her disposal and is available for driving the vehicles that the logistic manager administrates; and if a certain driver, e.g. because of alcohol consumption, cannot pass the authorization control and sobriety testing station, this situation can, at least from a pure operative perspective, basically be handled as a normal sick-leave and the driver's runs or trips are assigned to another driver. Thus, a distributed access control and sobriety testing system according to the invention simplifies planning and leads ultimately to a better use of resources. This is in contrast with a conventional system wherein a separate breath alcohol ignition interlock system is installed in each of the vehicles, and wherein there is always a risk that one driver cannot start the vehicle to which he/she was the designated driver. If the logistic manager administrates, for example, a fleet of buses, such a start-up failure typically leads to delays or even to cancellation of certain bus-rides, mainly because such a start-up failure occurs at the very last stage of a management procedure, i.e. typically at the point in time when the bus was already scheduled to set off.

The temporary authorization information can be issued and handled in many ways, for example: 1) the temporary authorization information is sent to and stored in the access control unit(s); 2) the temporary authorization information is stored in the central control unit and is accessible and retrievable by the access control unit(s); or 3) the temporary authorization information is transferred into a media, which herein is referred to as a temporary authorization information carrier, which the individual who seeks access transfers to the access control unit which he/she subsequently interacts with.

According to one aspect of the invention, in line with example 1) above, the access control unit receives and stores temporary authorization information and is operable to perform part of the access procedure as a stand-alone unit, i.e. without having to communicate with the central control unit during all steps of the access procedure. This represents an advantage in that the access procedure may be performed even if communication between the central control unit and the access control unit is lost, for example if the access control unit is a mobile unit and/or to reduce response times in the system.

A system for access control and sobriety testing comprises at least one authorization control and sobriety testing station, which can be a stationary or portable unit. In one embodiment, an authorization control and sobriety testing station is arranged as mobile phone, e.g. a smart phone, provided with an alco-sensor and, optionally, with a camera.

All communications occurring in a system according to the invention can be wired or wireless communications, as applicable; and the system can preferably be arranged as an automatically operating system which is operating automatically without any interaction with a human operator.

The invention relates further to a corresponding method for access control and sobriety testing, which method comprises the steps of storing general authorization information in a central control unit; obtaining authorization data from an individual seeking access by means of an authorization control and sobriety testing station; sending the authorization data from the authorization control and sobriety testing station to the central control unit; obtaining a bodily signature sample from the individual seeking access by the authorization control and sobriety testing station; analyzing the bodily signature sample in the authorization control and sobriety testing station for detecting presence of alcohol in the bodily signature sample; sending the result of the analysis from the authorization control and sobriety testing station to the central control unit; issuing temporary authorization information by means of the central control unit if there is a positive match between the general authorization information and the authorization data and no detection of alcohol (or detection of alcohol in a concentration which is below a predetermined and acceptable limit) as indicated by the result of the analysis; obtaining the temporary authorization information by at least one access control unit; verifying the validity of the temporary authorization information by means of the at least one access control unit; and granting access to the individual seeking access by the at least one access control unit, if there is a positive verification of the validity of the temporary authorization information.

As with the system for access control and sobriety testing, the method can apply three different operating principles for providing the at least one access control unit with the temporary authorization information, i.e. the temporary authorization information is sent from the central control unit to the at least one access control unit; the temporary authorization information is stored in the central control unit and is accessed and retrieved or otherwise read by the at least one access control; or the temporary authorization information is transferred from the authorization control and sobriety testing station into a temporary authorization information carrier, which the individual seeking access transfers to the at least one access control unit. Further, in a method for access control and sobriety testing, the authorization control and sobriety testing station can be at least partly integrated in a mobile phone, and the step verifying the validity of the temporary authorization information can comprise preferably the step of verifying the temporal validity of the temporary authorization information, and the bodily signature sample can be a breath sample or a transdermal alcohol detection, and the access control unit can be located in a vehicle, or located at a gate or barrier to a restricted area, wherein all these features can be incorporated separately or in combination in a method for access control and sobriety testing.

BRIEF DESCRIPTION OF THE DRAWINGS

The present invention will be further described and explained hereinafter by means of non-limiting examples and with reference to the appended drawings, wherein.

DETAILED DESCRIPTION

Figure 1:
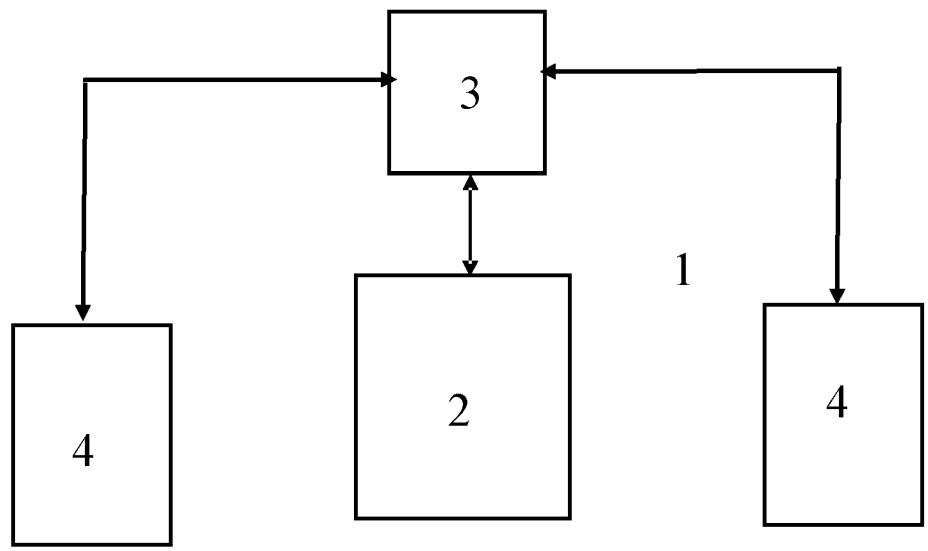
FIG. 1 shows the general outline of a distributed system for access control and sobriety testing according to the present invention.

FIG. 1 shows the general outline of a distributed access control and sobriety testing system 1 according to the present invention. The system 1 comprises an authorization control and sobriety testing station 2, a central control unit 3, and at least one access control unit 4 (in FIG. 1, two access control units 4 are shown). The central control unit 3 is configured and arranged to store general authorization information about the individuals or persons who potentially have access to the functions, areas, devices or units, e.g. vehicles, to which the system 1 is arranged to grant access. The general authorization information can include general information about the employees of a company, e.g. employment number, personal identification number, permitted working hours, access restrictions, etc., and also information about identification carriers, e.g. company identification cards or badges, issued by the company and linked to a specific employee. The general authorization information can further include biometrical identification information, for example in the form of finger prints, eye identification data, or facial recognition data.

The repetition rate of an authorization control and sobriety testing station, such as the authorization control and sobriety testing station 2, is typically one test in 5-10 seconds, whereas the throughput of an access control unit, such as the access control unit 4, is 5-10 times faster. The preset system architecture wherein these two functions are separated is therefore of great importance.

The authorization control and sobriety testing station 2 is configured and arranged to verify the identity of a person or individual who is seeking access by obtaining authorization data from this person or individual, who is seeking access to the functions, areas, devices or units, to which the system 1 is arranged to grant access. As a simple example, the individual seeking access can enter authorization data in the form of his/her employment number or personal identification number into the authorization control and sobriety testing station 2, which sends the authorization data (i.e. the employment number or the personal identification number) to the central control unit 3, which performs a matching procedure between the authorization data provided by the individual and the general authorization information which was previously stored in the central control unit 3. (Alternatively, authorization data can be provided in the form of biometrical data, e.g. a facial image, a finger print or eye identification data which the authorization control and sobriety testing station 2 obtains by scanning bodily parts of the individual seeking access.) If the central control unit 3 finds a match between the authorization data and the general authorization information (for example, that the employment number entered by the individual is listed among the employment numbers stored in the central control unit 3, or that the scanned facial image matches with a facial image previously stored in the central control unit 3) and if there are no applicable restrictions associated with the general authorization information, a positive match has been found. Such restrictions can be geographical restrictions; the individual is, for example, employed by the company but has not been permitted access to the specific premises or areas which he/she now attempts to enter. Other examples of restrictions can be time-dependent restrictions; the individual is, for example, only allowed to work day-time but has interacted with the authorization control and sobriety testing station 2 during night-time; or device-dependent restrictions; the individual is, for example, only permitted to drive company cars but has entered authorization data into an authorization control and sobriety testing station 2 located at the entrance of a bus garage.

The authorization control and sobriety testing station 2 is further configured and arranged to analyse a bodily signature sample, which is obtained from the individual who is seeking access to the functions, areas, devices or units, to which the system 1 is arranged to grant access, and configured and arranged to detect the presence of alcohol in the bodily signature sample. The bodily signature sample can be a breath sample, which the individual seeking access delivers to the authorization control and sobriety testing station 2 via, e.g., a mouthpiece arranged at or in the authorization control and sobriety testing station 2. Such systems are well-known in the art and their internal functions will not be further described herein. The breath analyzer can be contactless, using $CO_2$ determination to compensate for sample dilution, and enabling faster throughput by eliminating the need to attach mouthpieces. Infrared absorption is a preferred operating principle for an alcohol-detecting sensor, but electro-chemical detection is also possible. Another example of a bodily signature sample is a transdermal alcohol detection, wherein an individual places his/her finger tip on a translucent plate, whereupon the fingertip is, for example, laser-irradiated with infra-red light, and a device performs a spectroscopic analysis of light having passed the fingertip. Such a system is, for example, available from the company TruTouch Technologies. The distributed access control and sobriety testing system 1 is consequently preferably a non-invasive system for access control and sobriety testing, something which applies for all embodiments and examples presented herein.

The authorization control and sobriety testing station 2 is further configured and arranged to send the result of the analysis of the bodily signature sample to the central control unit 3, which, if there is a positive match between the authorization data and the general authorization information and no detection of alcohol, issues temporary authorization information, which is sent to, or which is otherwise accessible or obtainable by, the at least one access control unit 4. As used herein, the term "no detection of alcohol" includes detection of alcohol in an amount or concentration that is below a predetermined and acceptable level, which level may or may not be related to a legal limit; and by the term "sobriety" is meant that alcohol, i.e. ethyl alcohol, above a certain threshold concentration is not present in the blood or breath of a person or individual, wherein the threshold concentration may or may not be related to a legal limit. Further, in the case of a negative sobriety test, i.e. the test result indicates that alcohol above a certain threshold concentration is present in the blood or breath of a person, the person will not gain access unless subsequent investigations, which typically involve further sobriety tests, give a result showing that the person (now) is sober.

Figure 2:
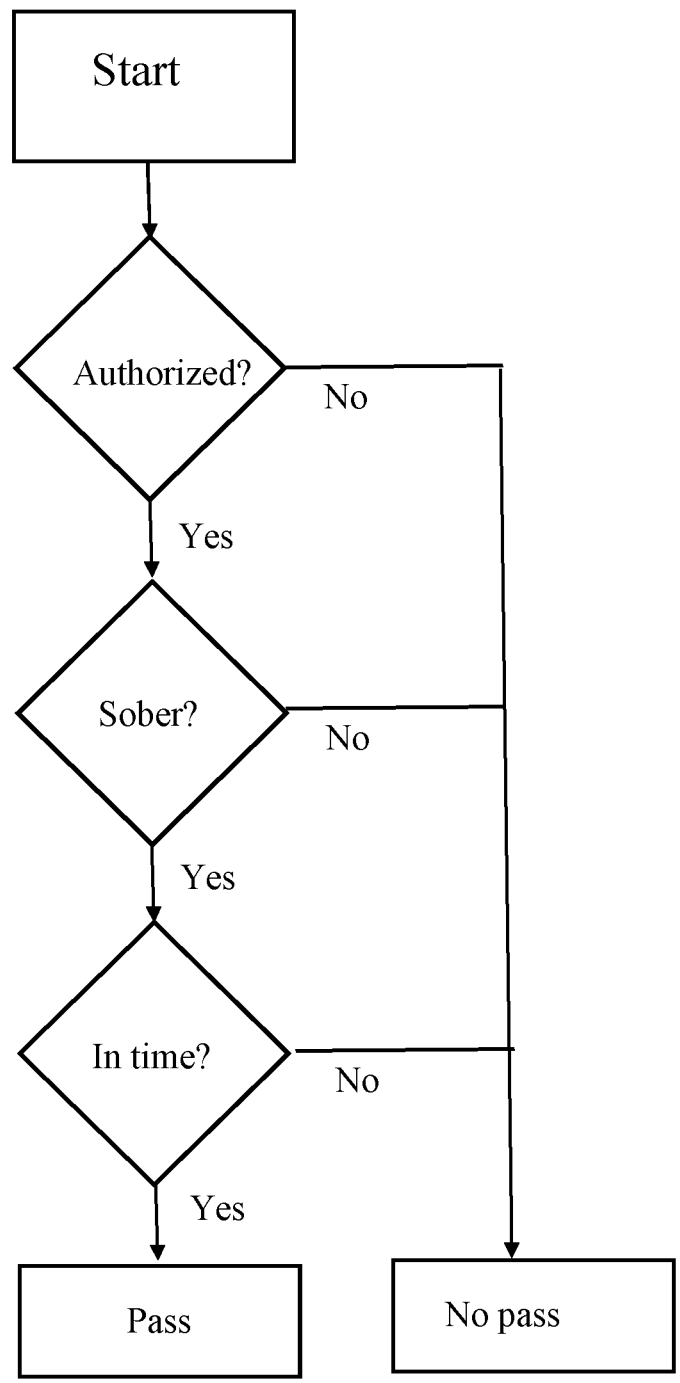
FIG. 2 shows a flowchart over a procedure for obtaining access in a distributed system for access control and sobriety testing according to the invention.

As described above, the at least one access control unit 4 is configured and arranged to obtain the temporary authorization information issued by the central control unit 3 and to verify the validity of the temporary authorization information, and to, if the temporary authorization information is valid, grant access to the individual who is seeking such access. The step of verifying the validity of the temporary authorization information comprises therefore at least verifying the temporal validity of the temporary authorization information, i.e. verifying that the temporary authorization information is still valid and was not issued a too long time ago. Thus, the access control unit 4 obtains a time indication for when the temporary authorization information was issued and compares this time indication with the current time as provided by an accurate clock, which can be an internal clock arranged in the access control unit 4 or an external clock arranged in, for example, the central control unit 3, and if the time indication is within a predetermined time interval from the current time, the individual is granted access by the access control unit 4. A flow chart over the general operating principle of the system 1 for access control and sobriety testing is shown in FIG. 2.

In one embodiment of the distributed system 1 for access control and sobriety testing, the at least one access control unit 4 is further configured to obtain authorization data from the individual seeking access and to match this authorization data with general authorization information, which typically is stored in the central control unit 3. The authorization data obtained by the access control unit 4 can be the same authorization data that already was provided by the individual when he/she was interacting with the authorization control and sobriety testing station 2, or the authorization data delivered to the access control unit 4 can be different authorization data. The authorization data obtained by the authorization control and sobriety testing station 2 can, for example, be employment number, whereas the authorization obtained by the access control unit 4 can be a finger print, or vice versa. The purpose of this second identity verification is the eliminate or at least minimize the risk that access is granted to a person who has got hold of the temporary authorization information in a non-legitimate way. A second identity verification procedure can be implemented in all embodiments and examples presented herein.

The present distributed system for access control and sobriety testing provides a number of advantages over systems in which an access control and sobriety testing unit is implemented as an individually operating, stand-alone device in one specific vehicle. It should, for instance, be appreciated that an access control unit, such as access control unit 4, operates much faster than an authorization control and sobriety testing station, such as authorization control and sobriety testing station 2, which not only has to handle authorization data but also must obtain and analyse a bodily signature sample, a procedure that takes several seconds and even minutes. With the present system for access control and sobriety testing, an authorization control and sobriety testing station can be placed in a location and environment where individuals tend to have more time to interact with a control and testing station, e.g. in a comfortable entrance area of a company building, whereas an access control unit is placed in the driver's vehicle, a place and situation in which the driver has already started his/her shift and is eager to drive off to comply with his/her schedule. An authorization control and sobriety testing station is typically also inherently more sensitive to external conditions, e.g. temperature, than an access control unit, and with the present system for access control and sobriety testing, the authorization control and sobriety testing station can preferably be placed in an optimal and user-friendly place, whereas the access control units are placed in more "rough" environments, which can be located at long distances from the authorization control and sobriety testing station.

According to one aspect of the invention, the units requiring interaction with a user, the authorization control and sobriety testing station 2 and the access control unit 4 are provided at different locations. The user will first encounter the authorization control and sobriety testing station 2 at a first location and at a later stage encounter the access control unit 4 at a second location. The second location may for example be in a vehicle and the access control unit being a mobile unit that communicates with the central control unit 3 via wireless communication.

Further, the system 1 for access control and sobriety testing comprises at least one access control unit 4, and in FIG. 1, two access control units 4 are schematically depicted, but it is to be understood that the system 1 can comprise any number of access control units 4. In one embodiment of the invention, an access control unit 4 is implemented in a vehicle; and the system 1 for access control and sobriety testing can, for example, be used by a logistic manager to administrate and handle a fleet of vehicles, each of which is equipped with a specific access control unit 4, as was exemplified and discussed above with reference to a fleet of buses. When an access control unit 4 is implemented in a vehicle, the term "access" means allowance to enter or start the vehicle in question. The term "access" can also mean allowance to enter an area, which can be a more or less restricted area, including premises and public buildings; and an access control unit can, for example, be installed in a road barrier or gate. Road barriers that are equipped with an alcohol sensor are well-known in the art and are sometimes referred to as "alcogates". However, also these alcogates operate individually as stand-alone arrangements, which implies that if one driver of one vehicle is not allowed to pass the alcogate, queues and other traffic congestions are likely to arise, which will negatively affect other drivers. Also, as was indicated above, the mere time to analyse a breath sample poses a potential traffic problem. There are also legal implications associated with alcogates since a potentially non-sober driver actually already is driving his/her vehicle when he/she attempts to pass the alcogate, and therefore the operation of an alcogate can require the presence of a police officer.

With the present distributed system for access control and sobriety testing, the problems associated with alcogates can be overcome, which will be demonstrated by the following, non-limiting example, in which a system according to the invention is used in combination with a road barrier or gate, which is located at the exit of a vehicular ferry or at some other place in a ferry harbor, such that all vehicles, or certain types of vehicles, such as lorries, must pass the barrier before they are allowed to finally leave the harbor area and drive off on connecting roads. In this ferry example, an access control unit is arranged in connection with the barrier, while an authorization control and sobriety testing station can be placed at the entrance to a vehicle deck of the ferry, wherein the authorization control and sobriety testing station in combination with a central control unit can issue temporary authorization information to all drivers who have entered valid authorization data into the authorization control and sobriety testing station and who have also provided a bodily signature sample, which, upon analysis by the authorization control and sobriety testing station, indicates that the driver is sober. Thus, all vehicles that are about to leave the ferry have a sober and (temporarily) authorized driver, and the access control unit arranged at a barrier located at an exit area from the ferry does only need to verify the validity of the temporary authorization information, i.e. to verify that the driver did not pass the authorization control and sobriety testing station a too long time ago. By this arrangement, there are no unnecessary delays related to the time taken to analyse a breath sample or other bodily signature samples, and there are less risks of traffic problems related to problems caused when a potentially non-sober driver attempts to pass the barrier and is refused to do so, and also legal implications are less severe since a driver who is not sober is stopped already at the entrance to the vehicle deck, i.e. before he/she actually is driving a vehicle.

A system for access control and sobriety testing can according to the invention be implemented in many ways. Thus, in the embodiment described above in conjunction with FIG. 1, a central control unit 3 was schematically depicted as a separate unit, remote from the authorization control and sobriety testing station 2. It is, however, possible to integrate parts or functions of a central control unit into an authorization control and sobriety testing station, or to completely integrate a central control unit into an authorization control and sobriety testing station. Such a system 11 for access control and sobriety testing is schematically disclosed in FIG. 3, where an authorization control and sobriety testing station 12 comprises a central control unit 13—as indicated by the dashed lines—which communicates with at least one (here two) access control unit 14. All functions of the integrated central control unit 13 are, however, from a functional viewpoint identical with the ones of the central control unit 3 described above with reference to FIG. 1, and an access control and sobriety testing system according to the invention will herein be described with explicit reference to a central control unit even if the central control unit at least partly is integrated into an authorization control and sobriety testing station.

As has been described above, a central control unit issues temporary authorization information based upon a positive verification of the identity of an individual seeking access, i.e. a positive match between authorization data provided by the individual and the general authorization information stored in the central control unit, and no detection of alcohol, wherein the temporary authorization information subsequently is obtained by an access control unit. According to the invention, temporary authorization information can be issued in many ways, including but not limited to three operating principles: 1) the temporary authorization information is sent to the access control unit(s) and preferably stored in the access control unit(s); 2) the temporary authorization information is stored in the central control unit and is accessible and retrievable by the access control unit(s); or 3) the temporary authorization information is transferred into a media, which herein is referred to as a temporary authorization information carrier, which the individual who seeks access transports or otherwise transfers to the access control unit which he/she subsequently interacts with.

As an example of the first operating principle, being one aspect of the invention—in which temporary authorization information is sent to the access control unit(s)—, a central control unit sends the temporary authorization information in, for example, the form of the individual's employment number together with a time stamp, which indicates when the temporary authorization information was issued, i.e. the point in time when the individual entered correct authorization data into the authorization control and sobriety testing station and also provided a bodily signature sample showing that the individual was not under the influence of alcohol. The access control unit receives and stores the temporary authorization information, and when the individual subsequently interacts with the access control unit, he or she is requested to enter his/her employment number, and the access control unit matches the employment number now provided by the individual with the employment numbers already stored in the access control unit and if a positive match is found, the access control unit compares the time stamp associated therewith with the current time as given by an accurate clock, e.g. an accurate internal clock, and if the difference between the time given by the time stamp and the current time is within a predetermined time interval, which can be pre-programmed or be sent together with the temporary authorization information, the individual is granted access. In employing this principle of operation the access control unit 4 is operable to perform part of the access procedure as a stand-alone unit, i.e. without having to communicate with the central control unit during all steps of the access procedure. An advantage with this first operating principle is that the access control unit is operative even if the communication between the access control unit and the central control unit is interrupted. Another advantage is that if the temporary authorization information cannot be transferred to the access control unit, the central control unit is informed that a certain access control unit is at least temporary malfunctioning and actions can be taken.

As first example of the second operating principle, being one aspect of the invention—in which temporary authorization information is stored in the central control unit and the access control unit accesses the central control unit and retrieves the temporary authorization information—, the central control unit links the temporary authorization information to the general authorization information. This temporary authorization information can then be a time indication. In this case, the individual seeking access provides authorization data, e.g. employment number or personal identification number, to the access control unit, which obtains the temporary authorization information, i.e. the time indication from the central control unit, by matching the authorization data with the general authorization information and determines the validity of the temporary authorization information by comparing the time indication with the current time given by an accurate clock, which can be an internal clock in the access control unit or an external clock located in, for example, the central control unit; and if the time indication is not more than a predetermined time interval before the current time, the temporary authorization information is determined to be valid, and the access control unit grants access to the individual seeking such access.

As a second example of the second operating principle, the central control unit also links the temporary authorization information to the general authorization information. This temporary authorization information can then be a time dependent digital flag or variable, which has a certain value before the end of a predetermined time-period and another value after the end of this predetermined time period. In this case, the individual seeking access provides authorization data, e.g. employment number or personal identification number, to the access control unit, which accesses the central control unit and obtains the temporary authorization information, i.e. the current value of the time-dependent digital flag, by matching the authorization data with the general authorization information and determines the validity of the temporary authorization information by comparing the current value of the time-dependent flag with a preset value, which can be an internal value stored in the access control unit or an external value stored in, for example, the central control unit; and if the current value matches the preset value, the temporary authorization information is determined to be valid, and the access control unit grants access to the individual seeking such access.

As a third example of the second operating principle, the central control unit blocks or temporarily deletes the general authorization information when the temporary authorization information is not issued, e.g. when presence of alcohol was detected, for a predetermined time period. Thus, the access control unit can only find and have access to the general authorization information during the time period it is valid. In other words, the existence, readability or accessibility of the general authorization information constitutes the temporary authorization information. In this case, the individual seeking access provides authorization data, e.g. employment number or personal identification number, to the access control unit, which accesses the central control unit and tries to match the authorization data with the general authorization information. If the access control unit finds and matches the authorization data with the general authorization information, the temporary authorization information is determined to be valid, and the access control unit grants access to the individual seeking such access.

An advantage with the second operating principle is that the validity of temporary authorization information easily can be changed; it can, for example, be discovered that the general authorization information for a specific individual is outdated or erroneous, or the temporal validity of the temporary authorization information can easily be changed if, for example, there is a general delay such that individuals who have passed an authorization control and sobriety testing station cannot go to an access control unit within the normal time span. Further, failures to pass an authorization control and sobriety testing station can, for example, provide information about excessive alcohol use among certain employees, or repeated unsuccessful attempts to get access to areas or vehicles can be indicative of illegal activities. Thus, appropriate actions, which may or may not be directly related to the operation of the system for access control and sobriety testing, can more easily be taken in a system that operates in accordance with the second operating principle.

As an example of the third operating principle, being a further aspect of the invention—in which temporary authorization information is transferred into a temporary authorization information carrier, which the individual who seeks access transfers or transports to the access control unit which he/she subsequently interacts with—, the authorization control and sobriety testing station delivers temporary authorization information to a temporary authorization information carrier, which in a simple case can be in the form of a time-stamped ticket, which the individual seeking access transfers to an access control unit, which obtains the time information by reading the time stamp from the ticket and verifies the validity of the ticket and thereby the validity of the temporary authorization information by comparing the time provided by the time-stamp with the current time given by an accurate clock, which can be an internal clock in the access control unit or an external clock located in, for example, the central control unit; and if the time indicated by the time-stamp is not more than a predetermined time interval before the current time, the temporary authorization information is determined to be valid, and the access control unit grants access to the individual seeking such access. In this embodiment, the temporary authorization information is preferably printed on a ticket at the authorization control and sobriety testing station as a bar code or QR code, or equivalent, and is readable by the access control unit. The use of a ticket provides redundancy to other communication channels and means for the temporary authorization information.

Other examples of temporary authorization information carriers are RFID cards, mobile phones, e.g. so-called smart phones, and similar devices that can receive and at least temporary store temporary authorization information issued by an authorization control and sobriety testing station, which temporary authorization information subsequently can be read by an access control unit. Another example is that an authorization control and sobriety testing station on a screen displays a code, which an individual who is seeking access reads and remembers until he/she enters the same code into an access control unit. In this case, the individual is the temporary authorization information carrier. An advantage with a system for access control and sobriety testing that operates in accordance with the third operating principle is that a person who illegitimately tries to obtain temporary authorization information issued for another person must get hold on the temporary authorization information carrier, which typically is an action that is noticed by that legitimate holder of the temporary authorization information.

Figure 3:
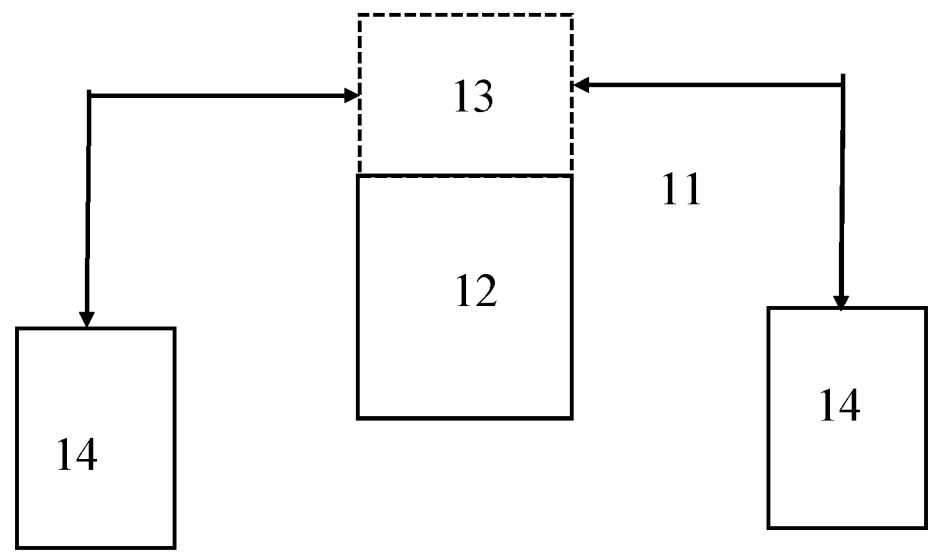
FIG. 3 shows the general outline of a distributed system for access control and sobriety testing, wherein a central control unit is at least partly integrated in an authorization control and sobriety testing station.
Figure 4:
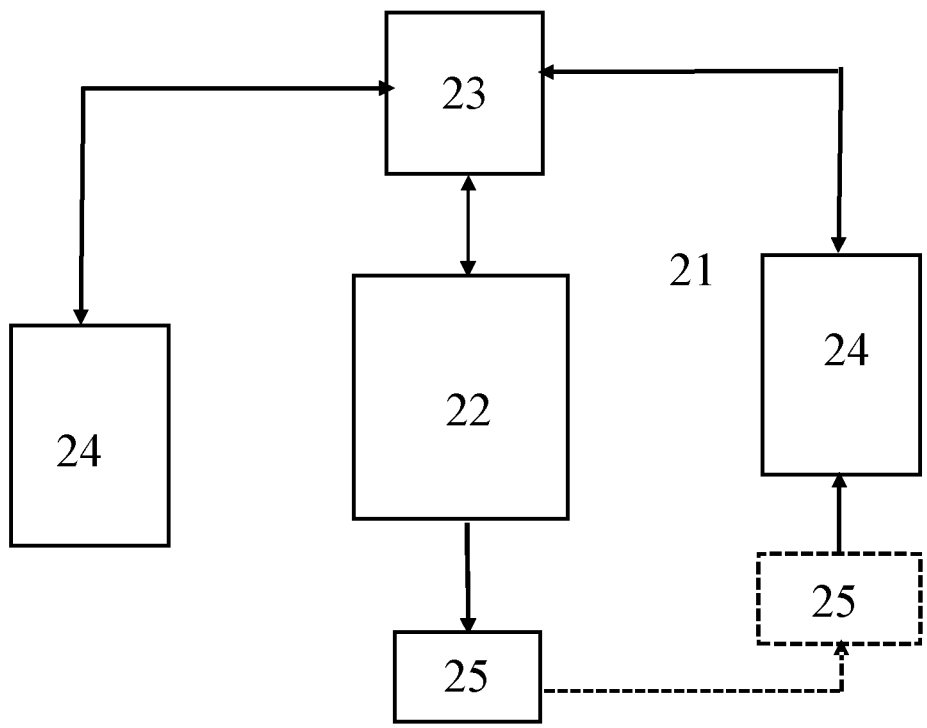
FIG. 4 shows the general outline of a distributed system for access control and sobriety testing which operates according to a third operating principle.

Systems operating in accordance with the first and second operating principles are illustrated in FIG. 1 and FIG. 3, and the general outline for a distributed access control and sobriety testing system 21 which operates in accordance with the third operating principle is schematically illustrated in FIG. 4, where the distributed access control and sobriety testing system 21 comprises an authorization control and sobriety testing station 22, a central control unit 23, and at least one (here two) access control unit 24. The authorization control and sobriety testing station 22 issues temporary authorization information based upon no detection of alcohol in a bodily signature sample provided by an individual seeking access and a positive verification of the authorization data provided by the very same individual, as has already been described above. FIG. 4 illustrates further that the temporary authorization information is transferred into a temporary authorization information carrier 25, which the individual who is seeking access transports to one of the access control units 24. When the individual is interacting with the access control unit 24, the access control unit 24 reads the temporary authorization information from the authorization information carrier 25, or the individual enters the temporary authorization information into the access control unit 24.

Figure 5:
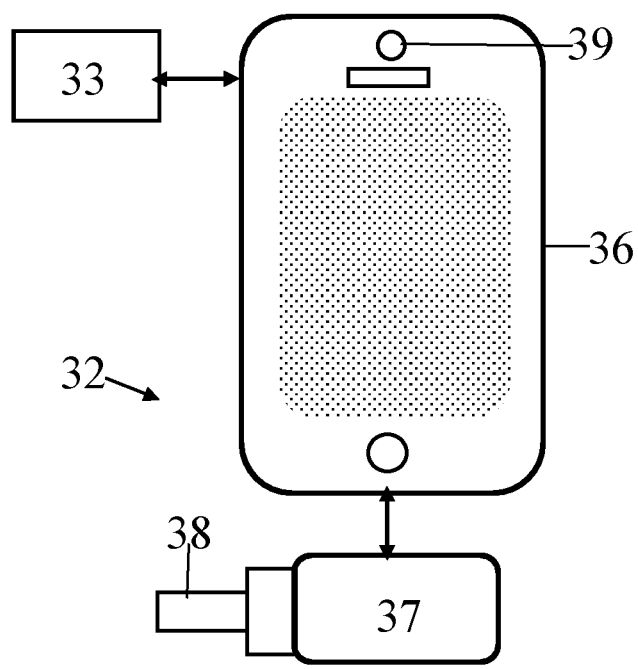
FIG. 5 shows an authorization control and sobriety station in the form of a mobile phone provided with a camera and connected to an alco-sensor.

In the examples given above and also illustrated in the figures, there have only been one authorization control and sobriety testing station. It should, however, be understood that a system for access control and sobriety testing according to the invention can comprise more than one authorization control and sobriety testing station. Further, the authorization control and sobriety testing station can be a stationary unit or a movable unit, including a portable unit, and an example of the latter is schematically illustrated in FIG. 5, wherein an authorization control and sobriety testing station 32 comprises a mobile phone 36 (e.g. a smart phone 36), which is connected to an alco-sensor 37, which is provided with a mouthpiece 38, into which an individual who seeks access delivers a breath sample. Alcohol detection system comprising a mobile phone are available, and an exemplifying system is the product iBAC sold by the company Alcosystems AB, Sweden, and another system is delivered by the company BACtrack, California, USA. (Alternatively, a mobile phone can be connected to a sensor for transdermal alcohol detection.) The authorization control and sobriety testing station 32 analyses the breath sample and sends the result of the analysis to a central control unit 33 together with authorization data. In this case, authorization data can be an identity number of the mobile phone 36 (which preferably is sent automatically when the mobile phone 36 interacts with the central control unit 33) if the identity number of the individual's mobile phone 36 is stored as general authorization information in the central control unit 33, or additional authorization data can be sent together with, or be sent before or after, the result of the breath analysis. In a preferred embodiment, the mobile phone 36 comprises a camera 39 by which a facial image can be taken and sent as authorization data to the central control unit 33, which compares the facial image with a facial image already stored therein. Further, if the result of the analysis is that there is no detection of alcohol and if a positive match can be found between the authorization data and the general authorization information, the central control unit 33 can send temporary authorization information back to the mobile phone 36, which then becomes the temporary authorization information carrier, i.e. the mobile phone 36 is part of a system that operates according to the third operating principle. It is, however, possible that the central control unit 33 sends the temporary authorization information to an access control unit (not shown in FIG. 5) in accordance with a system that operates according to the first operating principle, or the central control unit 33 can store the temporary authorization information such that the temporary authorization information is accessible by an access control unit (not shown in FIG. 5) in accordance with a system that operates according to the second operating principle. In the embodiment shown in FIG. 5, an authorization control and sobriety testing station 32 is completely integrated into a mobile phone 36 (e.g. a smart phone) in communication with an alco-sensor 37 and, optionally, provided with a camera 39. It is, however, within the scope of the invention to only partly integrate an authorization control and sobriety testing station in a mobile phone. In such embodiments, authorization data can, for example, by sent by a mobile phone whereas a bodily signature sample is entered into a dedicated station for sobriety testing. It is also possible to use a mobile phone provided with an alco-sensor and utilize an authorization control station to deliver authorization data.

With a distributed access control and sobriety testing system wherein an authorization control and sobriety testing station is at least partly integrated in a mobile phone, an individual can conveniently deliver authorization data and a bodily signature sample and can—if a positive verification of the authorization data is completed and there is no presence of alcohol in the bodily signature sample—obtain temporary authorization information before the individual approaches an access control unit. Such a person can, for example, be a taxi driver or a truck driver, who from home and via his or her mobile phone delivers authorization data and a bodily signature sample, and obtains temporary authorization information in return, and then within a predetermined time period interacts with an access control unit arranged in his/her taxi or truck, which can have been parked at the house or in a nearby parking place. Thus, a logistic manager operating a taxi or truck company gets information about the drivers who are available and can plan routes and trips and other operations accordingly, without the need for the drivers to physically appear at a specific place, such as a company building. Another exemplifying user of an authorization control and sobriety testing station integrated in a mobile phone is a boat or ferry passenger, who from his/her seat or cabin can delivery authorization data and a bodily signature sample via his/her mobile phone, and in return receive temporary authorization information, which he/she delivers to an access control unit located, for example, at the entrance to a vehicle deck or at a road gate located at the exit from the boat or ferry.

All communications occurring in a system according to the invention can, as applicable, be wired or wireless communications, and the system can preferably be arranged as an automatically operating system which is operating automatically without any interaction by a human operator. Redundant data communication channels can preferably be employed; for example by using combinations of telecommunication channels in the mobile 3G or 4G networks, and wireless communication via the internet using the TCP/IP protocol. Such a solution adds to the robustness of a system according to the invention. Further, all data communication is preferably encrypted, to obtain security against inappropriate monitoring.

In all embodiments and examples presented herein, an access control unit verifies the validity to the temporary authorization information associated with the individual who seeks access and interacts with the access control unit. This verification includes a verification of the temporal validity of the temporary authorization information, which means that the access control unit determines that the temporal authorization information was not issued a too long time ago before the individual started to interact with the access control unit, i.e. that authorization data and, in particular, the bodily signature sample were not delivered a too long time ago. To verify the temporal validity of the temporary authorization information therefore includes to determine that the temporary authorization information was issued within a predetermine time interval before the current time, i.e. the point in time when the individual starts to interact with the access control unit.

According to the invention, the time interval within which the temporary authorization information is valid, is determined and set by the operator of the system for access control and sobriety testing. In principle, any time interval can be set, but two different time intervals are envisaged as useful depending on the application of the system. If the system is implemented at a gate or barrier, such as a road barrier, which is located at the exit from, e.g., a ferry, a rather short time interval is presumably preferred, e.g. a time interval of about 10 minutes to 30 minutes (or 60 minutes), to give the individuals using the system enough time to transport themselves from an authorization control and sobriety testing station to an access control unit located at the road barrier. If the system instead is incorporated in a vehicle, a considerably longer time interval can be necessary. As an example, the system for access control and sobriety testing can be incorporated in vehicles driven by home-care personnel, who visit several clients at different places, and thereby have to stop and restart their vehicles repeatedly during a work shift. In this case, a suitable time interval can correspond to the length of the work shift, e.g. 4 hours or 8 hours, or somewhat longer to take into account unforeseen events.

With reference to FIGS. 1 to 5, a method for access control and sobriety testing, comprises the following steps: store general authorization information in a central control unit (3; 13; 23; 33); obtain authorization data from an individual seeking access by an authorization control and sobriety testing station (2; 12; 22; 32); send the authorization data from the authorization control and sobriety testing station (2; 12; 22; 32) to the central control unit (3; 13; 23; 33); obtain a bodily signature sample from the individual seeking access by the authorization control and sobriety testing station (2; 12; 22; 32); analyse the bodily signature sample in the authorization control and sobriety testing station (2; 12; 22; 32) for detecting the presence of alcohol in the bodily signature sample; send the result of the analysis from the authorization control and sobriety testing station (2; 12; 22; 32) to the central control unit (3; 13; 23; 33); issue temporary authorization information by the central control unit (3; 13; 23; 33) if there is a positive match between the general authorization information and the authorization data and no detection of alcohol; obtain the temporary authorization information by at least one access control unit (4; 14; 24); verify the validity of the temporary authorization information by the at least one access control unit (4; 14; 24); and grant access to the individual seeking access by the at least one access control unit (4; 14; 24), if there is a positive verification of the validity of the temporary authorization information.

In one embodiment of the method, the temporary authorization information is sent from the central control unit (3; 13; 33) to the at least one access control unit (4; 14), and in another embodiment, the temporary authorization information is stored in the central control unit (3; 13; 33) and is accessed and retrieved by the at least one access control unit (4; 14), and in still another embodiment the temporary authorization information is transferred from the authorization control and sobriety testing station (22) into a temporary authorization information carrier, which the individual seeking access transfers to the at least one access control unit (24). For all embodiments of a method according to the invention, the authorization control and sobriety testing station (32) can be at least partly integrated in a mobile phone (36), and the step of verifying the validity of the temporary authorization information can comprise the step of verifying the temporal validity of the temporary authorization information, and further, the bodily signature sample can be a breath sample or a transdermal alcohol detection, and the access control unit (4; 14; 24) can be located in a vehicle, or located at a gate or barrier to a restricted area.

Figure 6:
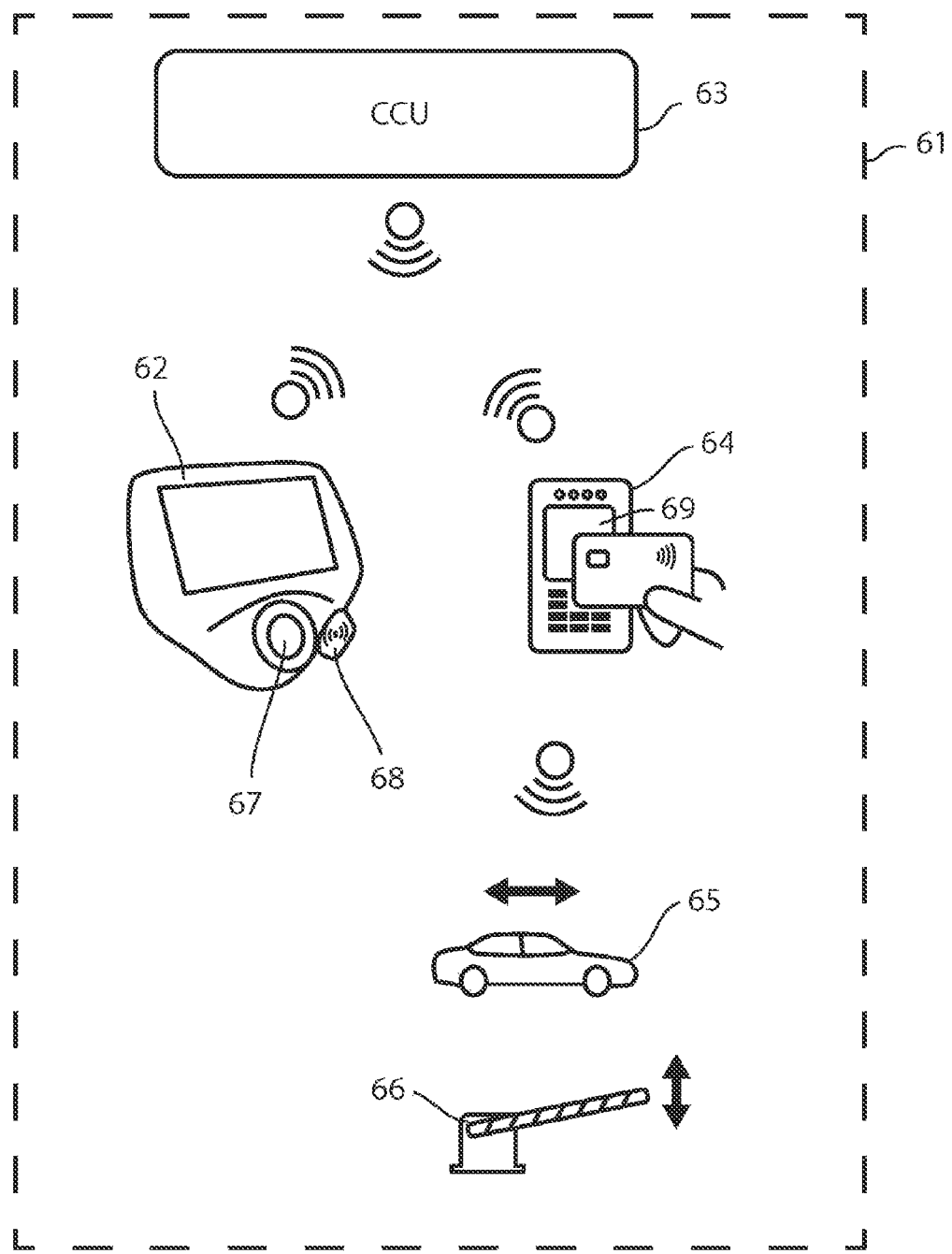
FIG. 6 shows schematically one embodiment of the invention.

FIG. 6 is a block diagram of one embodiment of the system 61 according to the invention illustrating the distributed characteristics of the system and its elements, including one authorization control and sobriety testing station 62, the central control unit 63, and one access control unit 64. For clarity, it is shown that bidirectional data communication between the units 62, 63, 64 is performed by means of wireless electromagnetic radiation in the radio frequency range as indicated by the radiation symbols between the units 62, 63, 64. These units may be physically separated and positioned arbitrarily since the wireless data communication is independent of their precise location. The authorization control and sobriety testing station 62 is equipped with a breath analyzer 67 for sobriety testing and a RFID (radio frequency identity) card reader 68 for authorization control. The central control unit 63 is basically a general-purpose server computer with high information throughput and capacity. The access control unit 64 includes a RFID card reader 69 and is controlling the mobility of a vehicle 65 or the access, e.g. passage, through a gate 66. The access control unit 64 is thus configured to have dual functionality. It is capable of controlling the mobility of a vehicle 65, the access through a gate 66, or both. The exact configuration of the units 62, 63 and 64 can change from one application to another since the individual units are identifiable.

The distributed system according to the invention and the embodiment illustrated in FIG. 6 is configured to allow near optimum efficiency and reliability. There are several optional technologies for wireless data communication, for example Bluetooth, Zigbee or LoRa platforms, the mobile telephone network, 3G to 5G, the internet, or a combination of these. The identity of units 62, 63, 64 within the system may be defined by individual IP (Internet Protocol) addresses, or a corresponding format. When connectivity is a major concern, the use of redundant data channels will maintain the system performance even if one channel is dysfunctional. The authorization control and sobriety testing station 62 and access control unit 64 are basically autonomous, and may perform their functions, including decision making based on consistent and preprogrammed rules, with less than 100% connectivity, since their operation is localized and depending only on the occasional data transfer and passage of persons seeking authorization or access. Data communication may be performed on these occasions or between them.

The system is configured to manage queuing between several persons seeking authorization or access simultaneously without loss of system performance. The high throughput of the access control unit 64 of less than one second between passages will minimize the risk for queuing at the critical point where a person needs quick and reliable access. The throughput of the authorization control and sobriety test station 62 is typically an order of magnitude slower, one test in 5-10 seconds. The distributed system is adaptable to this difference by using several authorization control and sobriety testing stations 62 in parallel.

Figure 7:
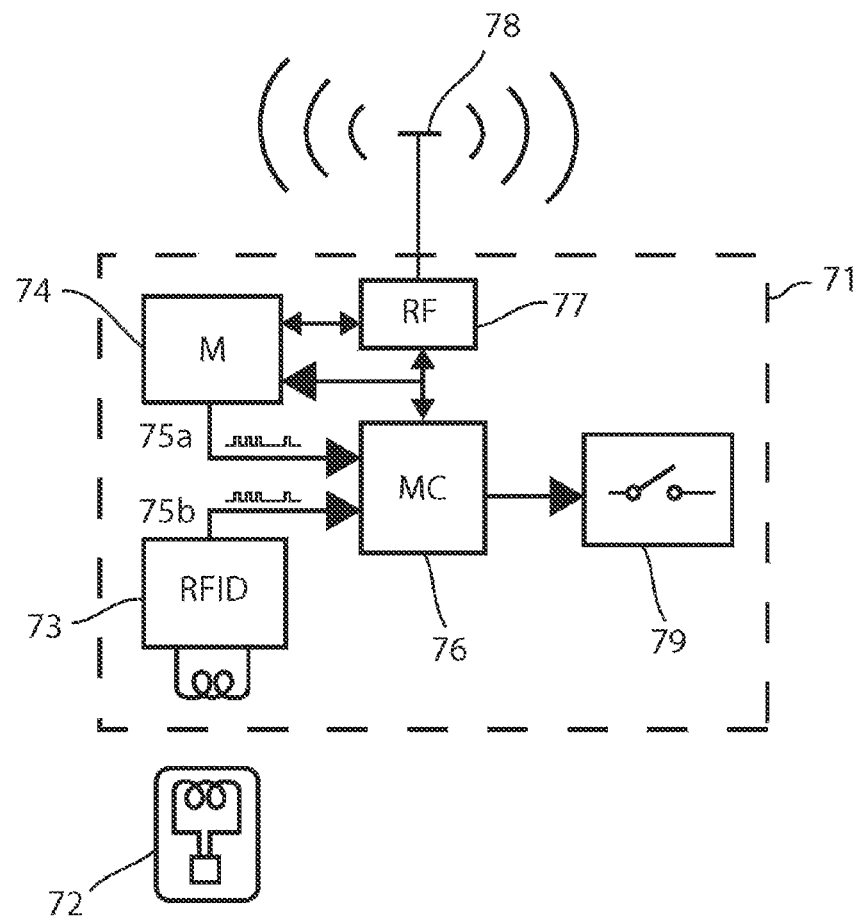
FIG. 7 shows schematically one embodiment of the invention.
Figure 8:
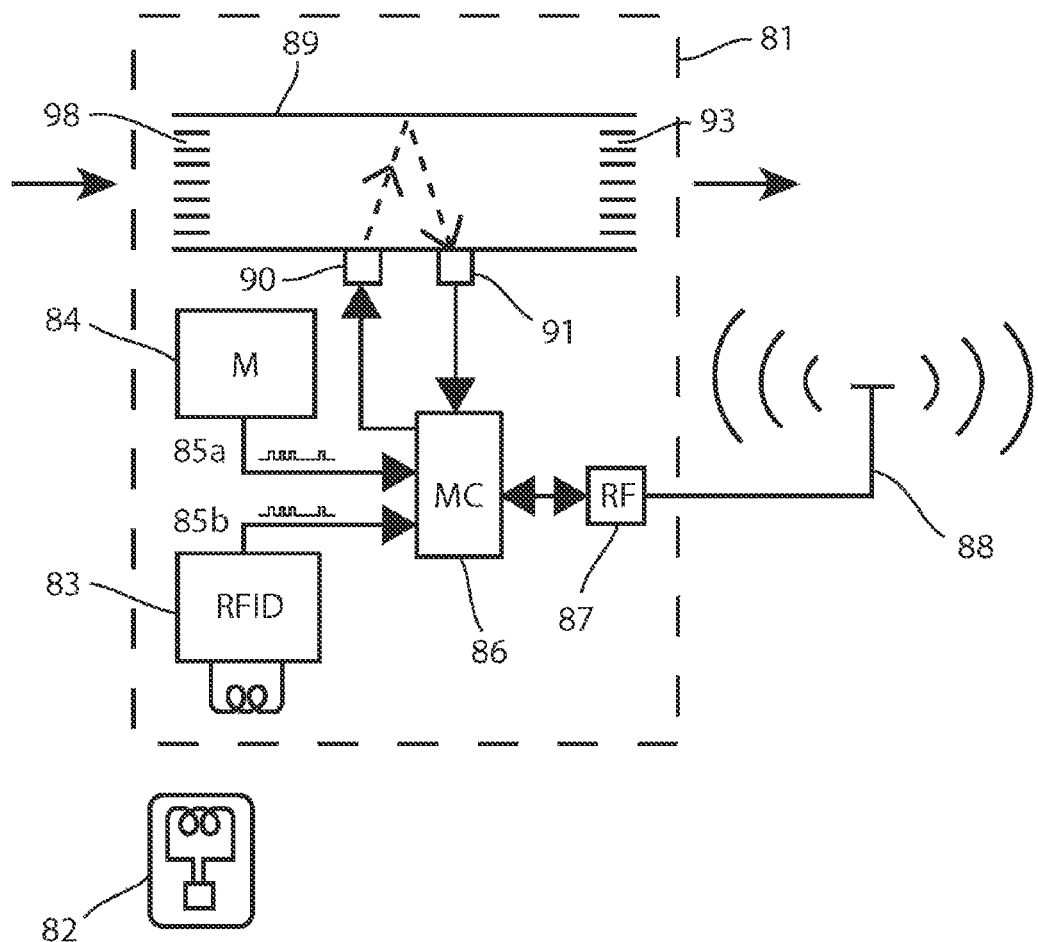
FIG. 8 shows schematically one embodiment of the invention.

FIG. 7 is a block diagram of one embodiment of the access control unit 71 according to the invention. The access control unit 71 includes one RFID card reader 73 configured to read information stored in a RFID card 72 when this card 72 is held in proximity to the card reader 73 by a person seeking access. A digital signature 75*b* is sent to a microcontroller 76, and compared with another digital signature 75*a* emitted from a memory device 74. When the digital signatures 75*a* and *b* are identical, the switch 79 is closing. The switching can be used to control the mobility of a vehicle or the access through a gate as previously described as a dual functionality in relation to FIG. 6. Also included is a radio frequency transceiver 77 including an antenna 78 by which the access control unit 71 is communicating bidirectionally with the central control unit. FIG. 8 is a block diagram of one embodiment of the authorization control and sobriety testing station 71 according to the invention. The unit includes one RFID card reader 83 configured to read information stored in a RFID card 82 when this card 82 is held in proximity to the card reader 83 by a person seeking authorization. A digital signature 85*b* is sent to a microcontroller 86, and compared with another digital signature 85*a* emitted from a memory device 84. When the digital signatures 85*a* and *b* are identical, the authorization control has been passed, and the person is commanded to provide a breath sample to the breath analyzer 89.

The breath analyzer 89 includes an infrared emitter 90 and detector 91 tuned to respond to specific infrared absorption bands of an intoxicating substance, for example alcohol. The infrared beam is passing through the breath analyzer 89 as indicated by the transverse dotted line reflected on the upper wall of the breath analyzer 89. The air flow corresponding to the breath sample is indicated by the flow direction from the inlet 92 to the outlet 93. The physical transport of breath samples and their wash-out between tests is the main reason for the authorization control and sobriety test station 62, 81 to have much lower throughput than the access control unit 64, 71.

In the absence of intoxicating substance above a certain limit concentration, temporary authorization information is issued to the person based on the observed sobriety by the breath analyzer 89 and the authorization information supplied by identification via the RFID reader 83.

Also included in the authorization control and sobriety testing station 81 is a radio frequency transceiver 87 including an antenna 88 by which the station 81 is communicating bidirectionally with the central control unit.

Figure 9:
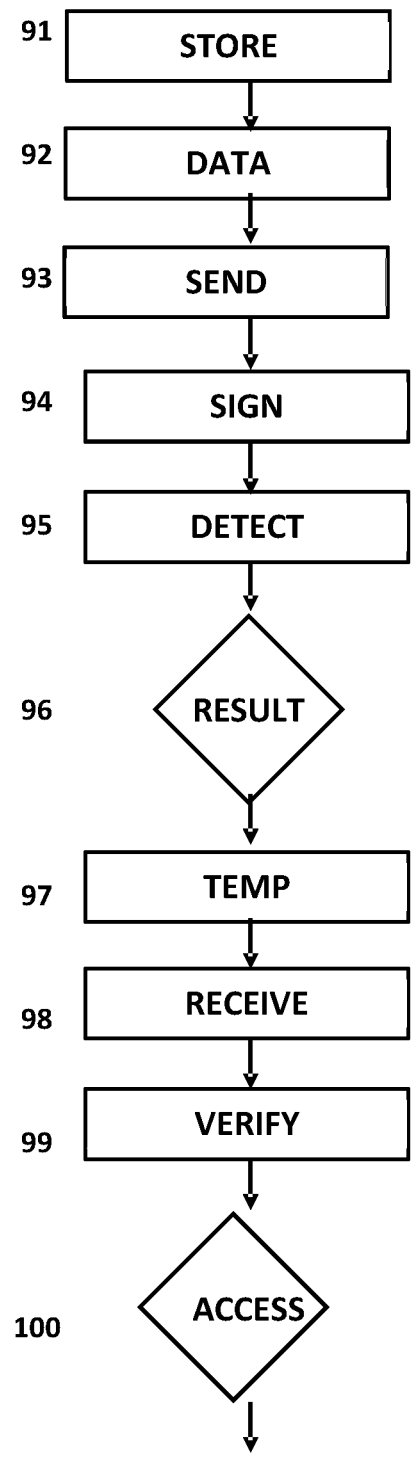
FIG. 9 is a flowchart over the method according to one embodiment of the invention.

FIG. 9 is a flowchart illustrating the method according to the invention involving the following distinctive steps:
In the first step 91, general authorization information is stored in the central control unit 3, 13, 23, 33, 63.
In the next step 92 authorization data is obtained from an individual seeking access by an authorization control and sobriety testing station 2, 12, 22, 32, 62, 81.
The next step 93 involves the transmission of the authorization data from the authorization control and sobriety testing station 2, 12, 22, 32, 62, 81 to the central control unit 3, 13, 23, 33, 63.
In step 94 a bodily signature sample is obtained from the individual seeking access by the authorization control and sobriety testing station 2, 12, 22, 32, 62, 81,
and the sample is analyzed for detecting the presence of alcohol in the bodily sample in step 95.
In step 96 the result of this analysis is sent from the authorization control and sobriety testing station 2, 12, 22, 32, 62, 81 to the central control unit 3, 13, 23, 33, 63.
Temporary authorization information is issued in step 97 by the central control unit 3, 13, 23, 33, 63 if there is a positive match between the general authorization information and the authorization data and no detection of alcohol.
In step 98 the temporary authorization information is received by one or several access control units 4, 14, 24, 64, 71.
In step 99 the validity of the temporary authorization information is verified by one or several access control units 4, 14, 24, 64, 71, and
access is granted in step 100 to the individual seeking access if there is a positive verification of the validity of the temporary authorization information.

According to an alternative embodiment of the method of the invention temporary authorization information issued in step 97 by the central control unit 3, 13, 23, 33, 63 to a temporary authorization information carrier. In step 99 the validity of the temporary authorization information is verified by an access control unit 4, 14, 24, 64, 71 based on the information from the temporary authorization information carrier, and access is granted in step 100 to the individual seeking access if there is a positive verification of the validity of the temporary authorization information.

A number of embodiments and implementation examples has been described above with reference to the system according to the invention. These embodiments and implementation examples are relevant also for the method of the invention and the modifications to the method straightforward for the skilled person given the teaching on the system level above.

Although the present invention has been described with reference to specific embodiments and examples, also shown in the appended drawings, it will be apparent to those skilled in the art that many variations and modifications can be done within the scope of the invention as described in the specification and defined with reference to the claims below.

The invention claimed is:

1. A distributed system for access control and sobriety testing, comprising a central control unit, in which general authorization information is stored, an authorization control and sobriety testing station, and at least one access control unit, wherein
   the authorization control and sobriety testing station is configured to obtain authorization data provided by an individual seeking access and to send the authorization data to the central control unit,
   the authorization control and sobriety testing station is configured to analyse a bodily signature sample provided by the individual seeking access and to detect the presence of alcohol in the bodily signature sample, and to send the result to the central control unit,
   the central control unit is configured to issue temporary authorization information based on a positive match between the general authorization information and the authorization data provided by the individual seeking authorization and no detection of alcohol,
   the authorization control and sobriety testing station and the access control unit are provided at different locations and arranged so that a user will first encounter the authorization control and sobriety testing station at a first location and at a later stage encounter the access control unit at a second location, and
   the at least one access control unit is configured to obtain the temporary authorization information and to verify the validity of the temporary authorization information, and to, based on a positive verification, grant access to the individual seeking access.

2. The system according to claim 1, wherein the validity of the temporary authorization information is the temporal validity of the temporary authorization information.

3. The system according to claim 1, wherein the system for access control and sobriety testing is a non-invasive system.

4. The system according to claim 3, wherein the bodily signature sample is a breath sample or a transdermal alcohol detection.

5. The system according to claim 1, wherein parts and/or functions of the central control unit are integrated into the authorization control and sobriety testing station.

6. The system according to claim 1, wherein the system for access control and sobriety testing is an automatically operating system.

7. The system according to claim 1, wherein the access control unit is located in a vehicle, or located at a gate or barrier to a restricted area.

8. The system according to claim 1, wherein the authorization control and sobriety testing station at least partly is integrated in a mobile phone.

9. The system according to claim 1, wherein the access control unit is further configured to obtain authorization data from the individual seeking access and to send the authorization data to the central control unit, which verifies the authorization data by matching the authorization data with the general authorization information.

10. A method for access control and sobriety testing, comprising the following steps:
    store general authorization information in a central control unit;
    obtain authorization data from an individual seeking access by an authorization control and sobriety testing station;
    send the authorization data from the authorization control and sobriety testing station to the central control unit;
    obtain a bodily signature sample from the individual seeking access by the authorization control and sobriety testing station;
    analyse the bodily signature sample in the authorization control and sobriety testing station for detecting the presence of alcohol in the bodily signature sample;
    send the result of the analysis from the authorization control and sobriety testing station to the central control unit;
    issue temporary authorization information by the central control unit if there is a positive match between the general authorization information and the authorization data and no detection of alcohol;
    obtain the temporary authorization information by at least one access control unit;
    verify the validity of the temporary authorization information by the at least one access control unit, wherein the authorization control and sobriety testing station and the access control unit are provided at different locations and arranged so that the individual will first encounter the authorization control and sobriety testing station at a first location and at a later stage encounter the access control unit at a second location; and
    grant access to the individual seeking access at the second location by the at least one access control unit, if there is a positive verification of the validity of the temporary authorization information.

11. The method according to claim 10, wherein the temporary authorization information is sent from the central control unit to the at least one access control unit.

12. The method according to claim 10, wherein the temporary authorization information is stored in the central control unit and is accessed and retrieved by the at least one access control unit.

13. The method according to claim 10, wherein the temporary authorization information is transferred from the authorization control and sobriety testing station into a temporary authorization information carrier, which the individual seeking access transfers to the at least one access control unit.

14. The method according to claim 10, wherein the authorization control and sobriety testing station is at least partly integrated in a mobile phone.

15. The method according to claim 10, wherein the step of verifying the validity of the temporary authorization information comprises the step of verifying the temporal validity of the temporary authorization information.

16. The method according to claim 10, wherein the bodily signature sample is a breath sample or a transdermal alcohol detection.

17. The method according to claim 10, wherein the access control unit is located in a vehicle, or located at a gate or barrier to a restricted area.

18. The method according to claim 15, wherein the temporary authorization information includes a time indication for when the temporary authorization information was issued.

19. The method according to claim 18, wherein the step of verifying the temporal validity of the temporary authorization information includes comparing the time indication with the current time.

* * * * *